United States Patent [19]

Meisch

[11] 4,305,405
[45] Dec. 15, 1981

[54] URINE METER BAG

[75] Inventor: Charles E. Meisch, Hasbrouck Heights, N.J.

[73] Assignee: C. R. Bard, Inc., Murray Hill, N.J.

[21] Appl. No.: 133,896

[22] Filed: Mar. 25, 1980

[51] Int. Cl.³ ............................................. A61B 5/00
[52] U.S. Cl. .................................. 128/762; 128/767; 128/768; 128/771; 73/219
[58] Field of Search ............. 128/762, 768, 771, 767, 128/295, 294; 4/144.1, 144.2, 144.3; 73/215, 219

[56] References Cited

U.S. PATENT DOCUMENTS

| | | | |
|---|---|---|---|
| 3,601,119 | 8/1971 | Engelsher | 128/767 X |
| 3,683,894 | 8/1972 | Villari | 128/767 |
| 3,776,231 | 12/1973 | Holbrook et al. | 128/768 X |
| 3,906,935 | 9/1975 | Raia et al. | 128/768 X |
| 3,961,522 | 6/1976 | Hanifl | 73/219 X |
| 4,095,589 | 6/1978 | Manschot et al. | 128/767 X |
| 4,178,934 | 12/1979 | Forman | 128/295 |
| 4,219,177 | 8/1980 | O'Day | 128/295 X |

Primary Examiner—Kyle L. Howell
Attorney, Agent, or Firm—Dennison, Meserole, Pollack & Scheiner

[57] ABSTRACT

A urine meter bag for accurately measuring and storing urine passing from a patient including a meter for receiving the urine flow having a large measuring chamber and a smaller calibrated chamber into which the flow initially passes. Upon filling of the calibrated chamber, overflow passes into the large chamber. The meter rests in tandem against a flexible drainage bag and is in fluid communication therewith near the top so that the meter can be tipped and its contents emptied into the bag. A special support assembly pivoted on the bag hanging bracket includes slotted side arms which straddle the meter and receive pivot pins on the meter which facilitate support and emptying of the meter into the bag.

9 Claims, 6 Drawing Figures

FIG. 2
FIG. 3
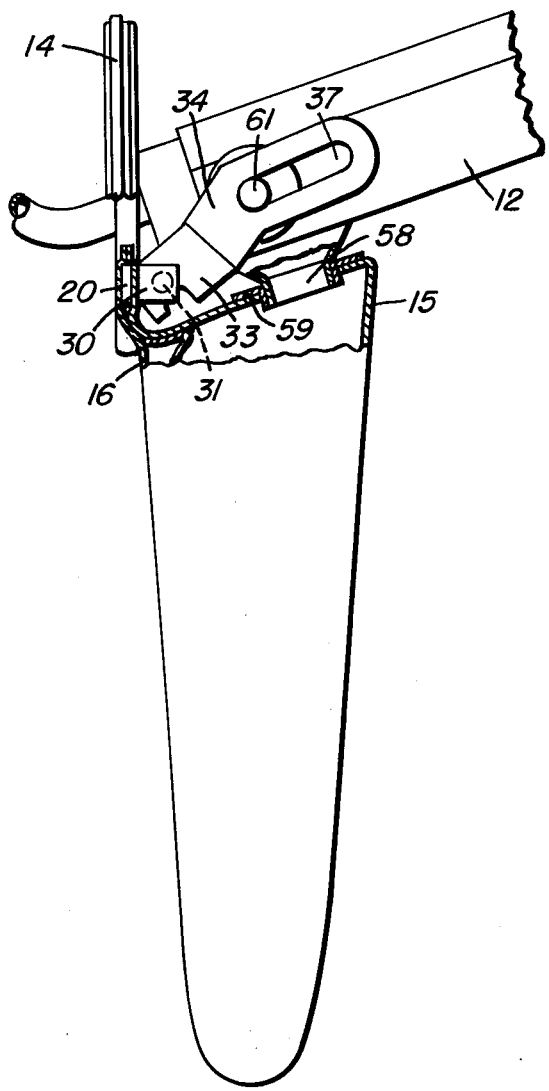
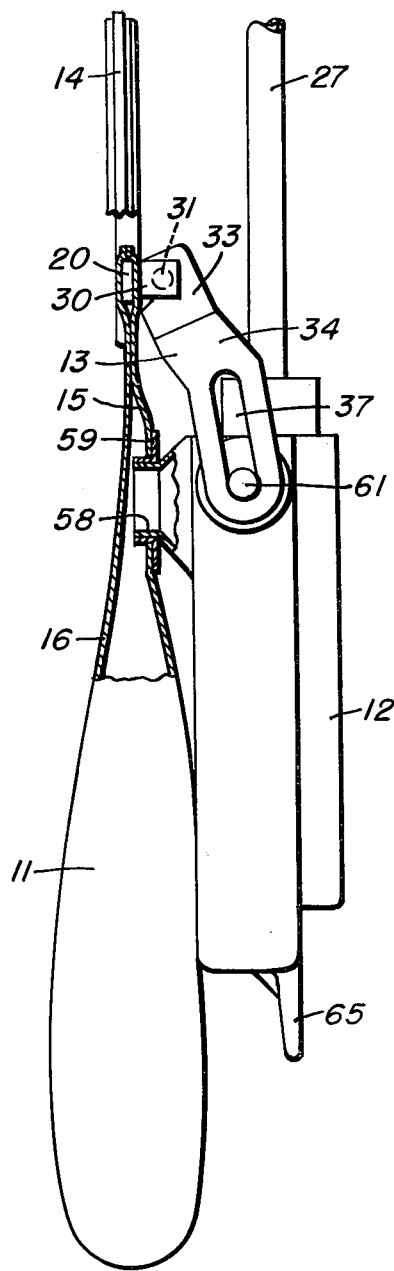

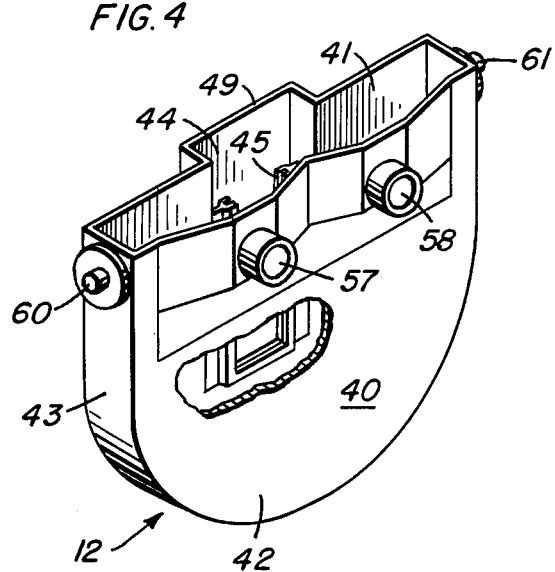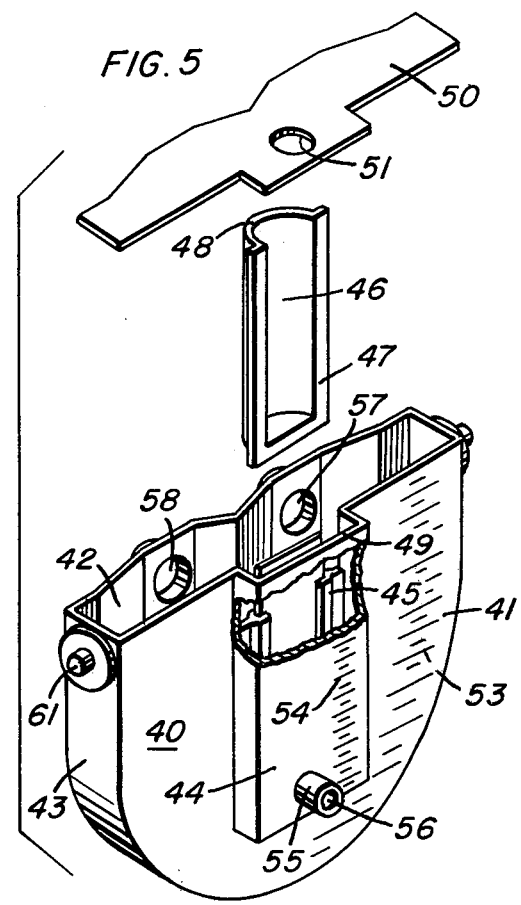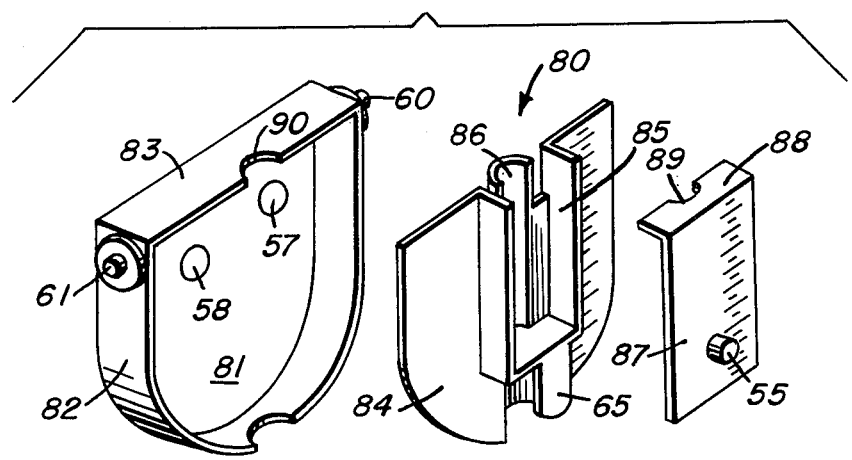

URINE METER BAG

BACKGROUND OF THE INVENTION

The present invention relates broadly to closed system urinary drainage bags of the type conventionally used in hospitals to collect urine from patients for the measuring of urine output and for urine sampling. Such bags are used routinely for post-operative patients as well as those with urological disorders. In use, the patient is first catheterized and the proximal catheter end then is connected to the drainage bag through a length of tubing. The bag is supported below the patient either from the bed rail or other support, and the urine drains by gravity from the patient through the catheter, the tubing and then into the bag.

More particularly, the invention herein relates to a novel urine collection bag having a novel metering receptacle attached thereto and a special support on the bag for the receptacle which permits and facilitates emptying of the receptacle contents into the bag from time to time.

Combination urine collection devices having meters are known in the art and are in present use. An early example of this combination is found in the U.S. Patent to Coanda, No. 3,345,980. In this construction, urine flows from a catheter into an elongated rigid meter, the lower end of which connects to a separate storage container. A pinch valve prevents transfer of urine to the container until desired, and a meter overflow line is also provided. The entire assembly occupies considerable space in use, is cumbersome and requires connecting the various parts.

Holbrook et al, U.S. Pat. No. 3,776,231, disclose a refined form of this combination and use two rigid containers located in tandem with a pivot valve joint which permits transfer of urine from a calibrated meter to a storage chamber.

Finally, Manschot et al, U.S. Pat. No. 4,095,589, disclose a flexible urine receptacle having a meter of rigid material fixed onto the face thereof and which may be tipped upwardly to discharge its contents into the receptacle. While this construction has the advantage of simplicity over the prior art, it still has disadvantages of inaccuracy and especially when the meter portion is fairly large, direct support thereof on the face of the bag can result in breakage with spillage of the contents.

The principal advantages of the present invention over the known prior art are the increased measuring accuracy due to the design of the calibrated meter and the additional strength and security achieved due to the new support system. Because of the large wall surface area within the meter portion of devices such as Manschot et al disclose, residual urine is left clinging to the walls of the meter after dumping. This residue will then flow down into the narrow bottom portion of the meter and will cause the subsequent meter reading to be in error and to indicate more urine output than the patient actually is producing.

SUMMARY AND OBJECTS OF THE INVENTION

A combined urine output meter and drainage bag is provided for use in collecting, sampling and measuring patient urine output. A rigid or semirigid urine meter has a centrally located narrow cross-section calibrated chamber into which urine flows directly from the patient, via catheter and flexible tube. This chamber provides for monitoring of small outputs, for example, up to 50 cc. Additional urine input will overflow this chamber into the main body of the meter which is designed to hold up to 300 cc of urine. Conduits are provided at the rear and near the top of the meter main body providing fluid flow communication to the interior of a preferably flexible drainage bag. Any accumulation of urine in the meter above its capacity will pass through the conduits to the drainage bag. A special support frame mounted on the bag carrying handle serves as a support for the meter and has a trunion and slot connection thereto to allow the meter to be tipped and emptied into the drainage bag at any time it is desired to begin a new flow measurement period.

It is a primary object of the present invention to provide a combination urine drainage bag and urine meter which will allow accumulation of large quantities of urine for measurement purposes and yet will permit improved accuracy in measuring small quantities of flow.

It is a further object of this invention to provide a support bracket for mounting a urine meter on a drainage bag which will allow the meter to be tipped in order to empty its contents into the bag.

It is a further object of this invention to provide a urine drainage bag and meter combination which is of simple construction, high accuracy, and is secure, reliable and safe in use and which may be used by nurses and technicians with a minimum of training.

A further object is to provide a urine drainage bag and meter combination which may be easily and inexpensively formed and assembled from plastic materials.

Various other objects and advantages of my invention will be readily apparent from the following detailed description taken in conjunction with the drawings in which an exemplary embodiment and a modified form of the invention are shown.

DESCRIPTION OF THE DRAWINGS

FIG. 2 is a side elevation of the urine drainage bag and meter partially in section and with the lower portion of the meter broken away and showing the meter in its tipped position for emptying into the bag.

FIG. 3 is a side elevation similar to FIG. 2 showing the meter in its normal use position on the bag.

FIG. 4 is a rear perspective of the urine meter casing with cover removed and a portion of the rear wall broken away to show interior detail.

FIG. 5 is an exploded front perspective of the urine meter assembly with part of the front wall broken away to show interior detail; and FIG. 6 is an exploded front perspective of a modified form of urine meter assembly.

DESCRIPTION OF A PREFERRED EMBODIMENT

Figure 1:
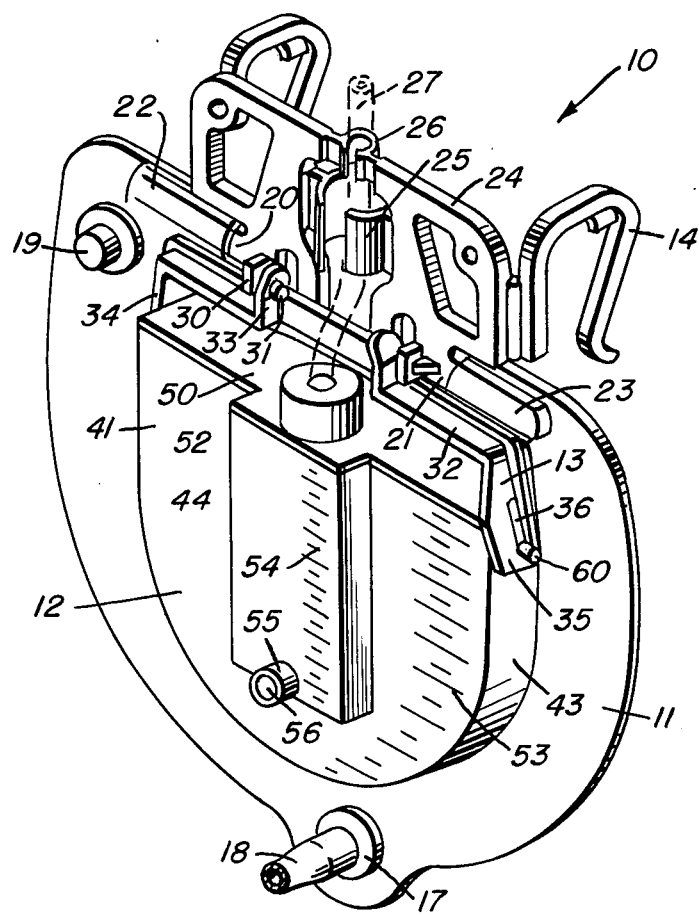
FIG. 1 is a perspective of the combined urine drainage bag and meter.

Referring now to the drawings, the urine meter bag of my invention is shown generally at 10 and includes a urinary drainage bag 11, a calibrated meter receptacle 12, a meter support subassembly 13 and a unitary hanger, hook, and handle assembly 14. Bag 11 is conventional and includes a front panel 15, a rear panel 16, both of fluid impervious sheet material such as polyvinyl chloride, which are heat sealed along their peripheral edge. The bag may also be provided with a drain 17 terminating in a latex tube 18 which may be clamped off in the well-known manner by a tubing clamp (not shown) or the like. Hence, bag 11 can be conveniently emptied from time to time as needed. Additionally, the front panel 15 may be provided with an air vent and bacteria filter 19 as is common in the art.

The urine meter bag may be transported, hung from an overhead support, or hooked over a bed rail by means of the assembly 14. This assembly is fully disclosed in and forms the subject matter of copending application Ser. No. 116,625 filed Jan. 29, 1980, by Meisch and Baker, and the disclosure therein is expressly incorporated herein by reference. The assembly 14 has support legs 20, 21 which are received in pockets 22, 23 formed on the bag.

Also integral with the central main frame 24 of assembly 14 is a receiving clip 25 for a drip chamber (not shown) and a circular split tubing collar 26 for receiving and retaining the inlet tube 27 which goes to the catheter.

Formed on the lower face of assembly 14 are bosses 30, each having an inwardly facing trunnion 31. The meter support subassembly 13 mounts on the trunnions and includes a cross member 32 having upwardly extending central tabs 33, each provided with a trunnion receiving aperture or cut-out and opposed downwardly extending side legs 34 and 35. The side legs each have a closed slot trackway 36 and 37 to support and guide the urine meter 12 when the same is in use and while it is being emptied into the bag 11. It will be apparent that the entire meter support subassembly 13 can be pivoted about the trunnions 31. It is also contemplated that the trunnions may alternatively be integral with the tabs 33 and appropriate apertures for trunnion reception provided in the bosses 30.

A preferred form of urine meter 12 construction is shown in FIGS. 1, 4 and 5, and is molded entirely of hard clear plastic such as cellulose propionate in three pieces. The meter housing 40 includes a front face 41 and rear face 42 and connecting side and bottom wall 43. While a rounded body shape is shown, the meter could be rectangular or any other desired shape. The front face 41 is centrally and forwardly extended to provide a calibrated chamber 44. Channel means 45 are molded on the inside of the meter housing 40 for reception of a curved chamber back wall 46 (FIG. 5) having outwardly directed flanges 47 on three sides. These flanges fit tightly into the channels 45 when the meter is assembled and may be sealed by heat, adhesives or the like. The top edge 48 of back wall 46 terminates below the top edge 49 of the chamber 44 as will be apparent later herein.

A flat cover member 50 is flush mounted over the housing 40 and has an aperture 51 overlying the calibrated chamber for the reception of the inlet tube 27. Here also cover 50 may be sealed to the housing in any known manner. A collar 52 as shown in FIG. 1 may fit about the inlet 27 to seal the aperture 51 if desired.

Appropriate indicia are inscribed as at 53 and 54, both on the front face of the meter housing 41 and also on the front face of calibrated chamber 44. The meter housing may have a total volume for example of from 250 to 300 cc, exclusive of the calibrated chamber which may have a volume of 50 cc. Any appropriate scale may be selected. By way of example, indicia 54 may represent 5 cc each, whereas indicia 53 may each represent 20 cc.

The inlet 27 passes directly into the calibrated chamber 44 and since this chamber terminates on its rear wall 46 at the top edge 48, any overflow will pass into the main meter housing 40. A very accurate record of urine output can be taken by adding together the readings from the scales 53 and 54.

A self-closing sampling port 55 is formed on the calibrated chamber 44. By insertion of a conventional syringe into the neoprene or the like plug 56, a desired measure of urine may be withdrawn for testing.

In order to provide interconnection for fluid flow between the urine meter 12 and the drainage bag 11, a pair of tubular ports 57 and 58 are mounted on rear face 42 of the casing 40. These ports are located above top edge 48 and immediately below cover plate 50. Appropriate apertures are provided in the front face 15 of the bag 11 to receive the ports and a flanged fitting 59 which is sealed to the front face 15. (FIGS. 2 and 3). In this manner, the meter is securely and permanently secured to the bag, however, as will be further described, its weight is not carried by this interconnection, but rather by the subassembly 13.

A pivot stub 60,61 is fixed on the side wall 43 of meter housing 40 adjacent the top edge thereof and these stubs are slideably and pivotally received within the slots 36 and 37. When the meter is in its normal use position as shown in FIG. 3, the entire weight of the meter is carried by the subassembly 13 through the stubs 60 and 61 which rest at the bottom of the slots 36 and 37 of the side arms 34 and 35. When it is desired to empty meter 12, it is tipped upwardly into the position of FIG. 2. A finger tab 65 near the bottom of the meter may be provided for this purpose. It will be noted that the top portion of the front face 15 of bag 11 will deform as shown and the stubs 60 and 61 will ride up within the slots 36 and 37. The meter cannot twist during tipping because of the lateral support offered by side legs 34 and 35, hence spillage is obviated. Upon release of the meter, it will again return to its FIG. 3 position. Numerous measurements of timed urine flow may be made in this manner until the bag 11 is nearly filled. Thereafter the bag may be emptied via outlet 17.

A modified urine meter is shown at 80 in FIG. 6 which operates in exactly the same manner as meter 12, however it is assembled using slightly different components. The bag wall element 81 includes integral side and bottom wall 82 and a top cover 83. The tubular parts 57, 58 and pivot stubs 60,61 are the same as in the preferred embodiment of FIG. 5. A front face plate 84 is sealed flush to the edges of element 81 and has the calibrated chamber 85 molded integrally therewith. The rear curved wall 86 coincides with the back wall 46 of the preferred embodiment. A chamber face plate 87 having a lip 88 at the top thereof is secured to chamber 85 in a flush manner to close it off. Note that semicircular recess 89 on the lip 88 cooperates with a similar recess 90 on cover 83 for reception of the inlet tube 47.

The manner of use of my new urine meter bag will be apparent from the foregoing, however it should be emphasized that the increased accuracy of my new meter is occasioned principally because of the small surface area of the calibrated chamber walls which eliminates residual urine buildup that flows down to the bottom as in Coanda and Manschot et al, noted supra. The assembly is designed as an expendable hospital supply that is used for but a single patient.

While cellulose proprionate has been noted as the material from which the meter is molded, other plastics such as cellulose acetate, cellulose butyrate, polyvinyl chloride and styrene could be employed. Similarly any conventional plastic film or sheet can be used in fabrication of the drainage bag.

I claim:

1. In a combination with a urine drainage bag, a urine meter having an inlet adapted for connection to a urinary catheter, said meter including a housing for storage and measurement of urine, said housing being in fluid communication near its top with said bag to permit emptying of the housing contents into the bag, and a small calibrated chamber within said housing and adapted to hold and measure a limited quantity of urine, said chamber receiving urine directly from said inlet, said chamber having a back wall within the housing, at least a portion of said back wall providing an overflow path to permit urine in excess of the chamber volume to pass into said housing, said drainage bag having a handle-support assembly adjacent its upper end, said meter being supported from said assembly and overlying said bag, and a U-shaped support bracket having opposed side legs pivotally mounted on said handle-support assembly, each side leg having an elongated substantially vertically oriented slot therein, said meter housing having two opposite side walls, each wall having an outwardly extended pivot stub, said stubs being received in said slots whereby said meter housing may be tipped upwardly to discharge its contents into said bag, said stubs riding upwardly in said slots and said support bracket pivoting on said handle-support assembly.

2. The combination as defined in claim 1, wherein said bag is formed of flexible plastic sheet and said meter is molded of rigid transparent plastic.

3. The combination as defined in claim 2 and further including scale measuring indicia on said meter housing and on said calibrated chamber.

4. The combination as defined in claim 3 and further including drain means adjacent the lower portion of said bag.

5. The combination as defined in claim 1 and further including a cannula pierceable self-sealing sampling port in said calibrated chamber for removing a sample of urine therefrom.

6. The combination as defined in claim 1, wherein the bottom of said calibrated chamber is spaced above the bottom edge of said meter housing.

7. The combination as defined in claim 1, wherein said bag is formed with at least one opening in its face, a short conduit extending from the rear face of said meter housing to each said opening, said conduit being securely sealed to said bag to provide said fluid communication.

8. The combination as defined in claim 1, wherein said meter has a top cover, a hole in said cover for passage of said inlet to said calibrated chamber.

9. In combination with a urine drainage bag, a urine meter having an inlet adapted for connection to a urinary catheter, said meter including a housing for storage and measurement of urine, said housing being in fluid communication near its top with said bag to permit emptying of the housing contents into the bag, a handle-support assembly secured adjacent the upper end of said bag, a U-shaped support bracket having opposed side legs pivotally mounted on said handle-support assembly, each side leg having an elongated slot oriented substantially vertically therein, said meter having two opposite side walls, each wall having an outwardly extending pivot stub, said stubs being received in said slots, said meter being supported from said bracket and overlying said bag, wherein said meter may be tipped upwardly to discharge its contents into said bag, said stubs riding upwardly in said slots and said support bracket pivoting on said handle-support assembly.

* * * * *